United States Patent
Bennett et al.

(10) Patent No.: US 6,245,034 B1
(45) Date of Patent: Jun. 12, 2001

(54) ADJUSTABLE RESISTANCE ORTHOPEDIC SPLINT

(75) Inventors: John Bennett, Rancho Palos Verdes; Willis C. Bradley, Gardena, both of CA (US)

(73) Assignee: Lenjoy Engineering, Inc., Gardena, CA (US)

( * ) Notice: Subject to any disclaimer, the term of this patent is extended or adjusted under 35 U.S.C. 154(b) by 0 days.

(21) Appl. No.: 09/170,878

(22) Filed: Oct. 13, 1998

(51) Int. Cl.$^7$ ........................................................ A61F 5/00
(52) U.S. Cl. .................................................. 602/20; 602/16
(58) Field of Search ...................... 602/5, 16, 20, 602/23, 26, 27; 128/881; 482/127; 623/59, 60, 50–52, 39; 601/33

(56) References Cited

U.S. PATENT DOCUMENTS

| | | | |
|---|---|---|---|
| 4,433,679 | * 2/1984 | Mauldin et al. | 602/26 |
| 4,485,808 | * 12/1984 | Hepburn | 602/5 |
| 4,657,000 | * 4/1987 | Hepburn | 602/16 |
| 5,013,037 | * 5/1991 | Stermer | 602/26 |
| 5,014,690 | * 5/1991 | Hepburn et al. | 602/16 |
| 5,395,304 | * 3/1995 | Tarr et al. | 602/26 |
| 5,437,619 | * 8/1995 | Malewicz et al. | 602/20 |
| 5,453,075 | * 9/1995 | Bonutti et al. | 602/16 |
| 5,472,410 | * 12/1995 | Hamersly | 602/16 |
| 5,624,390 | * 4/1997 | Van Dyne | 602/26 |
| 5,626,545 | * 5/1997 | Newman et al. | 482/124 X |
| 5,743,830 | * 4/1998 | Ho | 482/127 X |
| 5,814,000 | * 9/1998 | Kilbey | 602/16 |

* cited by examiner

*Primary Examiner*—Jerome W. Donnelly
*Assistant Examiner*—Denise Pothier
(74) *Attorney, Agent, or Firm*—Natan Epstein; Beehler & Pavitt

(57) ABSTRACT

An adjustable resistance orthopedic splint has two arms hinged to each other, each arm having two parallel spaced apart tubular segments joined by an application pad. A cable stretched between the arms is contained in the tubular segments and partially wrapped around the hinge. The cable is held under tension by an adjustable spring assembly to apply a variable torque urging the arms apart towards extension about the hinge.

20 Claims, 2 Drawing Sheets

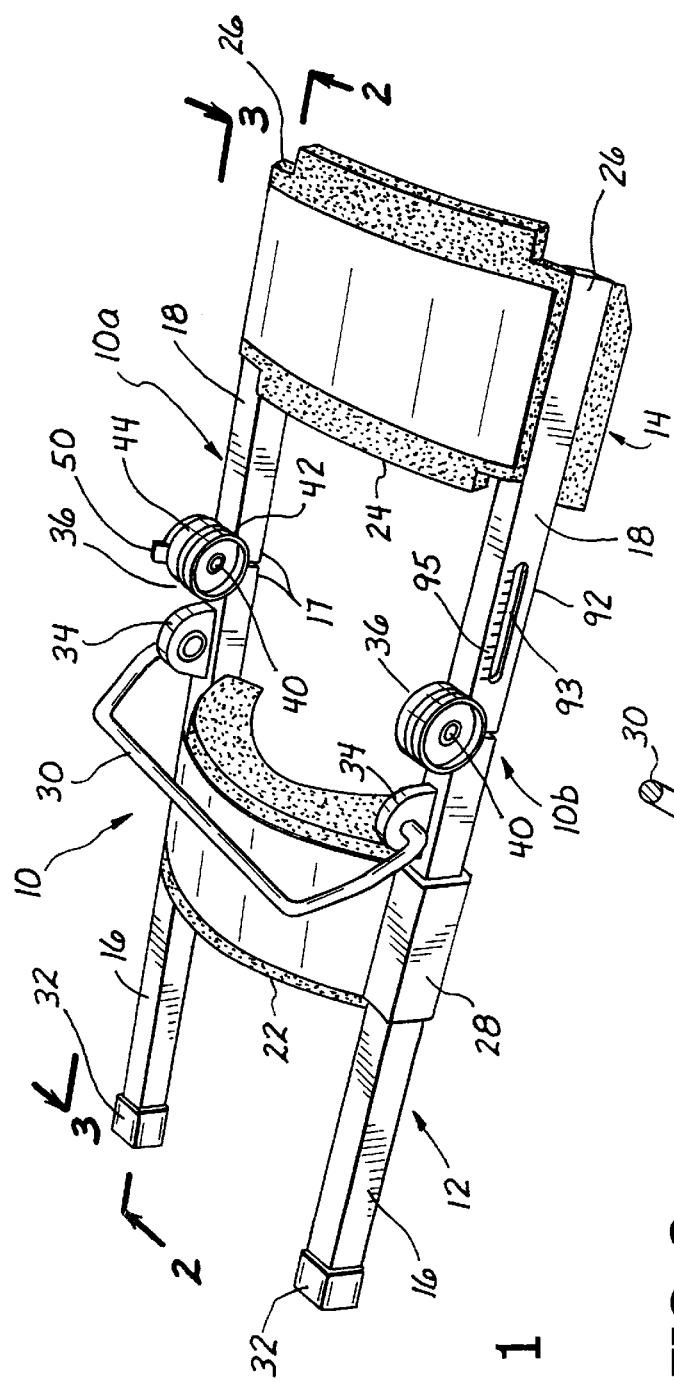
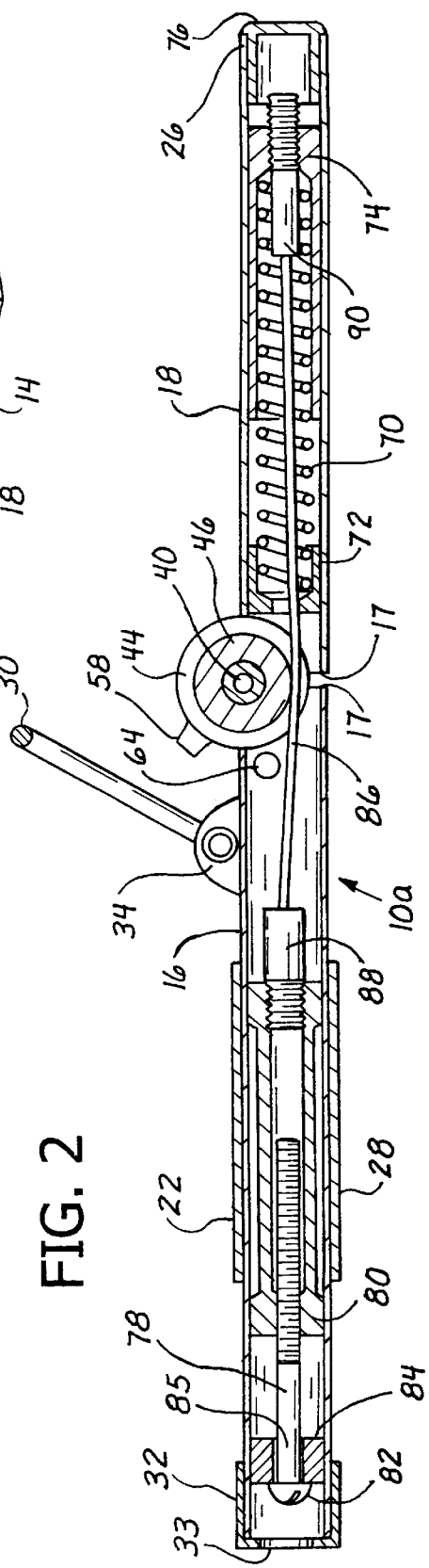

ADJUSTABLE RESISTANCE ORTHOPEDIC SPLINT

BACKGROUND OF THE INVENTION

1. Field of the Invention

This invention concerns orthopedic splints for application to the anatomical joint of a patient's limb for the purpose of limiting flexing of the joint during a period of medical rehabilitation, and in particular is directed to a torque splint which is spring loaded for extending the limb to which it is applied and offers an adjustable resistance to flexing of the joint for therapeutic purposes.

2. State of the Prior Art

Orthopedic torque splints have a variety of therapeutic applications. A primary application is to help long-term bedridden patients such as comatose individuals. Long term inactivity results in contraction of the muscles and consequent rigid retraction of the limbs. Properly applied torque splints are useful in resisting and reversing such retraction. A steady torque applied by the splint gradually pulls on the contracted muscles and extends the patient's limbs.

Existing torque splints suffer from a number of deficiencies which limit their usefulness and increase the cost of physical therapy. Among other shortcomings, presently available devices are typically restricted in the angular range settings, i.e. the arc of rotation permitted to the patient's joint, thus requiring more than one splint model or unit to satisfy all requirements. Furthermore, the actual torque resistance acting against retraction of the joint, for a given resistance setting of the device, typically varies over the arc of movement of the splint and therefore the true torque resistance acting at a given angular position of the splint cannot be readily determined. Commercially available torque splints using a cam action are an example of devices having actual torque values inconsistent with scale readings. Still further, presently available devices provide either no angle limiting feature or can be limited only in specific angular increments rather than continuously.

A continuing need exists for improved torque or resistance orthopedic splints which overcome these and other shortcomings of the prior art.

SUMMARY OF THE INVENTION

The present invention provides an adjustable resistance orthopedic splint which addresses the aforementioned shortcomings of the prior art. The improved splint has first and second arms hinged to each other for movement about a hinge axis between an extended position and a flexed or retracted position. A tensioning assembly contained in the arms of the splint applies an adjustable torque urging the splint arms towards an extended position. A goniometer assembly associated with the hinge of the splint may have continuously adjustable stops for limiting movement of the arms to any arbitrary lesser arc contained between maximally extended and maximally retracted positions of the splint.

In a presently preferred form of the invention, the splint arms are rigid tubular segments connected end-to-end by a hinge. The tensioning assembly includes a spring and cable assembly connected in tension between the two arms. Flexing of the splint arms wraps the cable around a hinge circumference arranged such that the tension on the cable tends to return the arms towards an extended position. The spring may be a coil spring with a coil axis transverse to the hinge axis and contained in one tubular arm segment, and connected by a cable to a tensioning block contained in the other tubular arm segment. The tensioning mechanism may include a screw adjustment in one of the arms for increasing or decreasing tension of the spring on the cable. A visual display indicative of the torque acting on the splint arms may be provided, such as a slot in the arm segment containing the compression block. The position of the compression block may then be read against a fixed scale on the arm segment. The spring and cable tensioning arrangement provides a consistently repeatable torque at any given scale reading regardless of the angle of the splint arms. This feature allows the torque to be accurately set by a therapist.

In the presently preferred form of the invention, the tensioning assembly includes a coil spring axially contained in a first of the tubular segments, a compression block longitudinally displaceable in the first of the tubular segments, a screw threaded for longitudinally displacing a tensioning block in a second of the tubular segments, and a cable connecting the tensioning block to the compression block, the first and second of the tubular segments being respectively on the first and second arms of the splint, such that tension on the cable acting to return the arms to an extended position can be adjusted by turning the screw.

One tubular segment in each hinged pair may be fixed for rotation with a hinge shaft and the other tubular segment in the pair may be rotatable about the shaft. The goniometer assembly on the shaft may include first and second stops individually rotatable about the shaft and a lock for fixing the stops at selected angular positions on the hinged shaft. Each of the stops may have a stop tab in angular interference with a detent mounted on the rotatable tubular segment, so that movement of the arms in extension and retraction can be limited to an arbitrary continuously adjustable arc by selective angular positioning of the stops.

In the basic or single sided splint each arm has one tubular segment, and suitable cuffs and/or retaining straps are provided for securing the splint arms to the upper and lower portions of a patient's limb.

A pair of single sided torque splints may be joined in side-by-side parallel relationship by means of pads elements so that the hinge axes of the joined splints are in approximately co-linear alignment with each other. First and second application pads may be provided on the arms of the joined splints, at least one of the two pads being slidably repositionable towards and away from the hinge axis of the splint. A swiveled handle may be attached across the joined splints to facilitate handling of the appliance by a therapist.

These and other advantages, features and improvements will be better appreciated and understood by reference to the following detailed description of the preferred embodiments taken in conjunction with the accompanying drawings.

BRIEF DESCRIPTION OF THE DRAWINGS

FIG. 1 is a perspective view of a double sided adjustable resistance orthopedic splint made by joining two single splints by means of transverse application pads;

FIG. 2 is a longitudinal section taken along line 2—2 in FIG. 1, depicting the tensioning assembly contained in the arms of each single splint for providing the adjustable resistance torque;

DETAILED DESCRIPTION OF THE PREFERRED EMBODIMENTS

Figure 3:
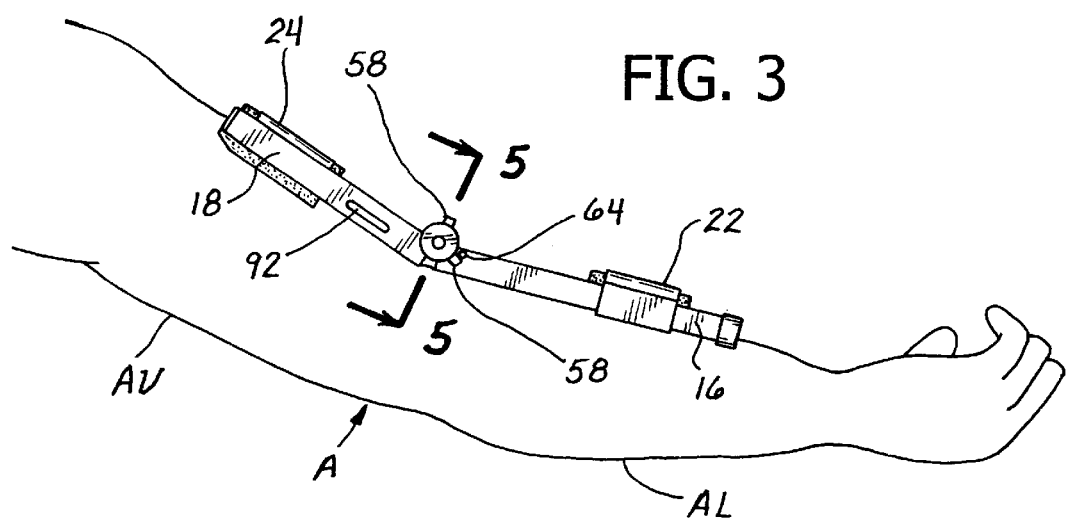
FIG. 3 illustrates a typical application of the orthopedic splint of FIG. 1 to an elbow joint, which is shown in an extended position.

With reference to the accompanying drawings in which like elements are designated by like numerals, FIG. 1 shows an adjustable resistance orthopedic splint generally designated by number 10. The torque splint 10 of FIG. 1 is a double splint which essentially consists of two single splints 10a, 10b, supported in parallel spaced-apart relationship by pads 22, 24. Single splints 10a, 10b are of generally similar construction and for simplicity the following description refers to splint 10a only, it being understood that splint 10b is similar unless otherwise stated.

Splint 10a has two arm segments 16, 18 each consisting of a length of rigid rectangular tubing, such as aluminum tubing. The two arm segments 16, 18 have inner ends 17 connected by a hinge 36 for movement about a hinge axis defined by hinge shaft 40. Extension of the splint arms occurs by rotation away from each other, while retraction involves folding the arms towards each other.

Figure 5:
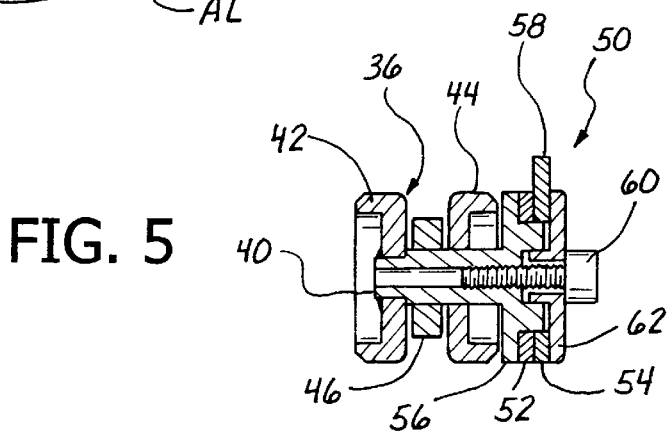
FIG. 5 is a sectional view taken along line 5—5 in FIG. 3, illustrating the construction of the hinge and goniometer assembly.

As shown in FIG. 5 hinge 36 includes a hinge shaft 40 welded to a fixed swivel disc 42, a swivel disc 44 rotatable on shaft 40, and a pulley 46 between the two swivel discs. Swivel disc 42 is welded to one tubular arm segment 18 while the other swivel disc 44 is welded to the other tubular segment 16. The inner ends 17 of the two arm segments are joined to the respective swivel discs 42, 44 of the hinge with the hinge axis offset to one side of the splint arms so that extension of the splint arms is limited by abutment of the inner ends 17 against each other, as best appreciated in FIG. 2, with the arm segments 16, 18 forming about a 180 degree angle between them. In this maximally extended position abutment of the inner ends 17 limits the arm segments against further downward rotation in FIG. 2 and the hinge axis 40 is offset above the fully extended tubular segments. Arm segments 16, 18 can retract by rotating upwardly on the hinge towards each other to a fully retracted position (not shown in the drawings) in which the arm segments 16, 18 are substantially folded together at about a zero angle to each other.

A variable torque resistance opposing retraction of the splint is provided by a tensioning assembly contained in the tubular segments 16, 18 of the splint 10a. The tensioning assembly shown in FIG. 2 includes a coil spring 70 which has a longitudinal axis aligned with the longitudinal dimension of tubular segment 18 on splint 10b. Spring 70 is axially contained in compression between an anchor block 72 fixed within the tubular segment 18, and a longitudinally slidable compression block 74. The other tubular segment 16 contains a longitudinally slidable tensioning block 80 and an anchor block 84 fixed in the tubular segment 16. A screw 78 passes through a bore 85 in the anchor block and is threaded into tensioning block 80. Screw head 82 makes an interference fit with the anchor block 84 and detains the screw axially against movement towards the hinged inner ends 17.

A cable 86 passes through the open inner ends 17 of the tubular segments and has one end connected to the tensioning block 80 and an opposite end connected to the compression block 74. One end of cable 86 is permanently fixed to a stub 88 threaded into the tensioning block 80. The other end of cable 86 is permanently fixed to another stub 90 threaded into the outer end of the compression block 74. As seen in FIG. 2, the cable 86 is stretched interiorly to tubular segments 16, 18 between the two stubs 88, 90 and consequently between the tensioning block 80 and compression block 74. Spring 70 acts against the sliding compression block 74, urging the compression block towards the outer end of arm 18b and keeping cable 86 in tension. An intermediate portion of the cable 86 generally tangentially touches the circumference of a pulley disc 46 which is of reduced diameter relative to the swivel discs 42, 44, so that the cable is held captive between the swivel discs. When the arm segments 16, 18 are rotated towards a retracted position from the fully extended position of FIG. 2 the cable wraps partially around the circumference of the pulley 46 because of the offset location of the hinge axis 40.

The resistance of the splint is adjustable by turning screw 78. This is accomplished by inserting a screwdriver through opening 33 end cap 32. Turning the screw in one direction has the effect of drawing the tensioning block 80 away from the coil spring 70, thereby pulling the compression block 74 towards anchor block 72 and further compressing the coil spring. Turning screw 78 in the opposite direction has the opposite effect, allowing the tensioning block 80 to be drawn toward the coil spring and permitting the coil spring 70 to push compression block 74 towards the end cap 76, thereby relaxing the spring and diminishing tension on cable 86.

The degree of compression of spring 70 is visually indicated by the position of the compression block 74 along a slot 92 cut in tubular segment 18, as best seen in FIG. 1. An index mark 93 on the compression block 74 can be conveniently read against a fixed reference scale 95 applied along the slot 92. This visual display provides an objective indication of the torque acting on the splint arms, allowing reliable and repeatable adjustments of the torque value by a therapist. In particular, the splint resistance can always be brought to a specific torque value for any angle of the splint arms 16, 18 by adjustment of screw 78. Furthermore, since the compression block slides back and forth in the arm segment 18 during retraction and extension of the splint, the torque display also provides an instantaneous display of the current torque value at any position of the splint arms through their arc of movement. The scale 95 can be directly calibrated in foot-pounds or other suitable force units.

The hinge 36 carries a goniometer assembly 50 which can be used to limit either extension or retraction, or both, of the splint. This is useful in implementing a therapeutic program involving gradual extension of a rigidly retracted limb. Extension of the limb by the steady torque may be limited to small increments to avoid possible damage to the joint being exercised. The goniometer assembly, best understood by reference to FIG. 5, includes two stop discs, 52, 54 rotatable on a shaft head 56 integral with hinge shaft 40. Each stop disc 52, 54 has a radially projecting stop tab 58. The two stop discs 52, 54 can be rotated independently of each other about the hinge shaft 40 so as to position the two stop tabs 58 at any desired angular relationship to each other. The two stop discs 52, 54 can then be fixed in a selected angular relationship by tightening a lock screw 60 to hold the two stop discs in a friction lock between the pressure disc 62 and shaft head 56. A detent pin 64, shown in FIGS. 2, 3 and 4 projects laterally from tubular segment 16 into angular interference with the two stop tabs 58. The goniometer assembly 50 is fixed relative to the tubular segment 18. The detent pin 64 is carried by tubular segment 16 on arm 12 of the splint 10a. Consequently, as the two arms 12 and 14 move between the extended position of FIG. 3 and the flexed position of FIG. 4, the detent pin 64 describes an arcuate trajectory concentric with the hinge shaft 40. The arcuate extent of this trajectory can be limited to any arbitrary arc lesser than 180 degrees by appropriate setting of the detent tabs 58. For example, in FIG. 3 the detent pin 64 is shown stopped against one stop tab arbitrarily designated 58a, which limits extension of the splint 10. In FIG. 4, the detent pin 64 is shown stopped against the other stop tab, arbitrarily designated 58b, which limits retraction of the splint to about a 90 degree angle, thereby limiting retraction of arm A to a similar angle.

The two single sided splints 10a, 10b are held in mutually parallel spaced-apart relationship by two application pads 22, 24 with the hinge axes 40 of the two single splints in substantially co-linear relationship to define a common hinge axis for the double splint 10. The two arm segments 16 form one arm 12 of the double splint, while the two arm segments 18 form the other arm 14 of the double splint. One application pad 24 is supported between and connects tubular segments 18 near free ends 26. The other application pad 22 is supported between tubular segments 16 on supports 28 which are longitudinally slidable along tubular segments 18 between end caps 32 and the hinge axis. A handle 30 is swiveled on swivel mounts 34 between tubular segments 16. The handle 30 is free to swivel through an arc in the direction of the tubular segments and provides a convenient grip for a therapist while applying or positioning the splint on a patient's limb.

Figure 4:
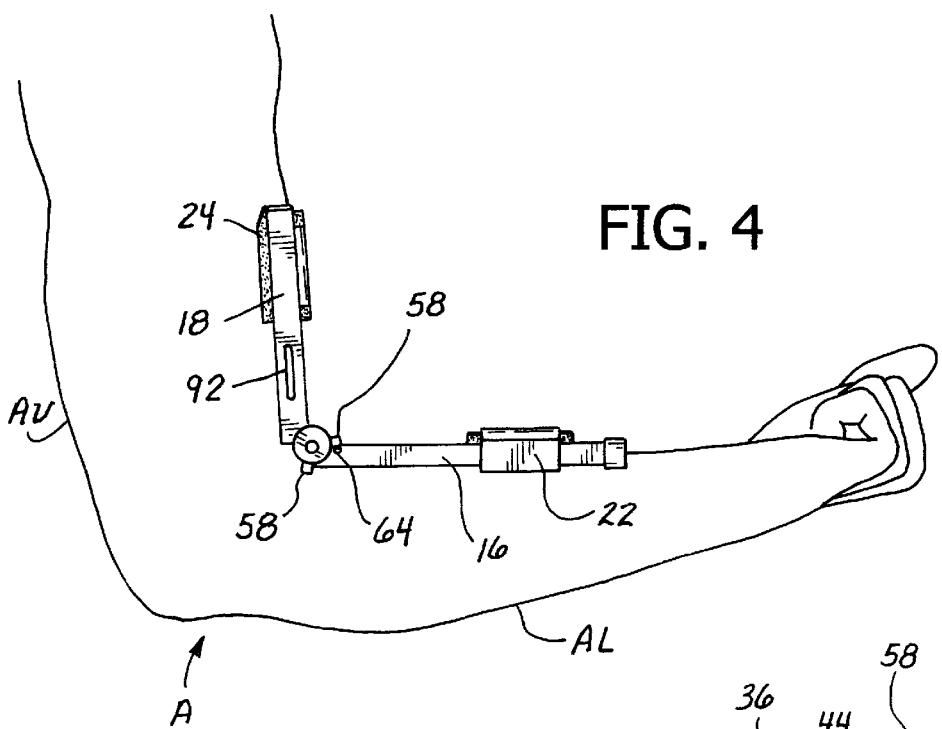
FIG. 4 shows the elbow joint and orthopedic splint of FIG. 3 in a partially flexed position.

FIG. 3 illustrates the manner in which the splint of FIG. 1 is applied to the anatomical joint of a human limb, an elbow joint in this example. A concave, limb contacting side of the application pads 22, 24 is applied respectively to upper arm AU and lower arm AL so that the hinge axis of the splint 10 lies approximately over the elbow joint on the inside of the arm A. When so applied the hinges 36 and goniometer 50 are raised on the retraction side of the splint and away from the patient's limb.

The splint of this invention, either in single sided or double sided form is secured to the patient's limb A by means of suitable arm cuffs and/or retaining straps wrapped over each of the two splint arms 12, 14 and around the upper and lower portions AU and AL of the limb A. The retaining straps are conventional to orthopedic splints in general and for clarity of illustration have been omitted in the drawings. Such straps are typically of moisture absorbent material such as cotton or terry cloth and have Velcro fasteners which secure the ends of the straps in place, all in a manner which is well understood in the art.

As presently preferred each side of the double splint 10, i.e., each splint 10a, 10b, includes a tensioning assembly such as shown in FIG. 2 and a single goniometer 50 on splint 10a as shown in FIG. 1. However, the double splint may also be constructed with a goniometer 50 on each hinge 36 and the tensioning assembly may be provided in only one of the splints 10a, 10b.

From the foregoing it will be appreciated that the adjustable resistance splint described above is of relatively simple yet rugged and dependable construction, is easily adjustable to a desired level of resistance, has a 180 degree range of movement and can be limited to any arbitrary lesser arc of movement by easy adjustment of the goniometer assembly. Although the foregoing description relates to an elbow splint, it is understood that the splint of this invention may be similarly applied to a knee joint.

While particular embodiments of the invention have been described and illustrated for purposes of clarity and example, it should be understood that many changes, substitutions and modifications to the described embodiments will be apparent to those having ordinary skill in the art without thereby departing from the scope of the invention as defined in the following claims.

What is claimed as new is:

1. An adjustable resistance orthopedic splint for application to the anatomical joint of a patient's limb, comprising:
    first and second arms, each of said arms having a pair of parallel spaced apart tubular segments joined by an application pad, said tubular segments on the first arm being hinged to said tubular ends on the second arm; and
    a spring assembly contained in at least some of said tubular segments and acting in tension between said arms to apply a torque urging said arms towards an extended position;
    said spring assembly comprising a coil spring contained in a first of said tubular segments, a compression block longitudinally displaceable in said first of said tubular segments, a screw threaded for longitudinally displacing a tensioning block in a second of said tubular segments, and a cable connecting said tensioning block to said compression block, said first and said second of said tubular segments being respectively on said first and second arms, whereby tension on said cable acting to return said arms to said extended position can be adjusted by turning said screw.

2. The orthopedic splint of claim 1 wherein said spring assembly comprises a cable connecting first and second tubular segments on said first and second arms, spring means operative for maintaining said cable in tension for urging said arms towards said extended condition, and screw means for increasing or decreasing said tension on said cable, whereby torque resistance to retraction of said arms is adjustable.

3. The orthopedic splint of claim 1 further comprising a handle connecting said pair of tubular segments on one of said arms.

4. The orthopedic splint of claim 3 wherein said handle is pivotably connected to each tubular segment in said pair such that the handle can be swiveled on said one of said arms.

5. An adjustable resistance orthopedic splint for application to the anatomical joint of a patient's limb, comprising:
    first and second arms, each of said arms having a pair of parallel spaced apart tubular segments joined by an application pad, said tubular segments on the first arm being hinged to said tubular ends on the second arm; and
    a spring assembly contained in at least some of said tubular segments and acting in tension between said arms to apply a torque urging said arms towards an extended position;
    wherein said tubular segments are in hinged pairs on a common hinge shaft, one tubular segment in said hinged pair fixed for rotation with said shaft and the other tubular segment rotatable about said shaft, and a goniometer assembly on said shaft, said goniometer assembly comprising first and second stops individually rotatable about said shaft and a lock screw for fixing said stops at selected angular positions on said shaft, said stops each having a stop tab in angular interference with a detent on said other tubular segment, whereby movement of said arms in extension and retraction can be limited to an arbitrary continuously adjustable arc by selective angular positioning of said stops.

6. An adjustable resistance orthopedic splint for application to the anatomical joint of a patient's limb, comprising:

first and second tubular segments defining two arms connected to each other by a hinge at adjacent ends of said segments;

an application pad attached to each of said tubular segments; and a cable contained within said tubular segments, said cable being connected at opposite ends to each of said tubular segments, a spring tensioning assembly fully contained in one segment for applying tension to said cable, a mid-portion of said cable wrapping around a pulley on said hinge thereby to apply a torque urging said arms towards an extended position about said hinge.

7. The splint of claim 6 wherein one end of said cable is connected to said tensioning spring assembly and an opposite end of said cable is connected to a tensioning block contained within another of said tubular segments and axially displaceable in said another of said tubular segments for continuously adjusting tension of said cable.

8. The splint of claim 6 wherein said spring tensioning assembly comprises an indicator visible exteriorly to said tubular segments for indicating instantaneous tension of said cable at any angular relationship of said tubular segments.

9. The splint of claim 8 wherein said indicator is linearly displaceable along one of said tubular segments.

10. The splint of claim 8 wherein said tension of said cable is continuously adjustable by turning a single threaded screw operative for axially displacing a tensioning block in one of said tubular segments.

11. The splint of claim 6 wherein said tensioning block is continuously adjustable over a tension range by turning a threaded screw element.

12. The splint of claim 6 wherein said application pads are continuously positionable along said tubular segments.

13. The splint of claim 6 wherein said application pads are continuously slidable along said tubular segments.

14. The orthopedic splint of claim 6 wherein said spring tensioning assembly comprises a coil spring contained in said first tubular segment between a compression block longitudinally displaceable in said first tubular segment and an anchor block fixed in said first tubular segment, a screw threaded for longitudinally displacing a tensioning block in said second tubular segment, said cable connecting said tensioning block to said compression block, whereby compression of said coil spring between said tensioning block and said anchor block can be adjusted by turning said screw thereby to change the tension on said cable acting to return said arms to said extended position.

15. The orthopedic splint of claim 14 wherein said coil spring has a coil axis transverse to an axis of said hinge.

16. The orthopedic splint of claim 6 further comprising stop means on said hinge continuously adjustable for limiting movement of said arms to any arbitrary arc contained between a maximally extended position and a maximally retracted position.

17. The orthopedic splint of claim 6 wherein said spring assembly may be set to achieve a desired torque value at any angular position of said arms between said extended position and a retracted position of said arms.

18. The orthopedic splint of claim 6, at least one of said application pad being slidably repositionable along one of said tubular segments towards and away from said hinge.

19. The orthopedic splint of claim 6 wherein each of said arms has a pair of parallel spaced apart tubular segments joined by one of the application pads attached to said tubular segments.

20. The orthopedic splint of claim 19 further comprising a handle connecting two said parallel spaced apart tubular segments on one of said arms transversely to said arms for use by a therapist while applying the splint to the said limb.

* * * * *